United States Patent [19]

Kremer et al.

[11] Patent Number: 5,029,999
[45] Date of Patent: Jul. 9, 1991

[54] LASER RADAR DEVICE

[75] Inventors: Richard M. Kremer, Poway; Eric I. Korevaar, San Diego, both of Calif.

[73] Assignee: Thermo Electron Technologies Corp., San Diego, Calif.

[21] Appl. No.: 456,975

[22] Filed: Dec. 26, 1989

Related U.S. Application Data

[63] Continuation-in-part of Ser. No. 422,671, Oct. 17, 1989, Pat. No. 4,983,844.

[51] Int. Cl.[5] .......................... G01C 3/08; G01P 3/36
[52] U.S. Cl. ..................................... 356/5; 250/336.1; 250/382; 356/28.5
[58] Field of Search ................. 250/336.1, 382; 356/5, 356/28.5

[56] References Cited

U.S. PATENT DOCUMENTS

| | | | |
|---|---|---|---|
| 4,024,396 | 5/1977 | Hill et al. | 250/338.1 |
| 4,167,329 | 9/1979 | Jelalian | 356/28.5 |
| 4,600,840 | 7/1986 | Chutjian | 250/336.1 |
| 4,822,164 | 4/1989 | Breen | 356/28.5 |
| 4,919,536 | 4/1990 | Komine | 356/28.5 |

OTHER PUBLICATIONS

Abreu, V. J.; Ap. Optics, vol. 18, No. 17, Sep. 1979.
Holmes, et al., Remote Sensing of Atompsheric Words Using Speckle Turbulence, A CO$_2$ Laser and O. H. Detector, Ap. Opt., vol. 27, Jun. 15, 1988.
Robert Menzies, Remote Lidar Atmospheric Wind Sensors, Comparative Performance etc., Ap. Op., vol. 25, No. 15, Aug. 11, 1986.
Kavaya et al., Remote Wird Profiling with Solid State Nd;YAG Coherent Lidar System, Op. Let., vol. 14, No. 15, Aug. 1, 1989.

Primary Examiner—Stephen C. Buczinski
Attorney, Agent, or Firm—John R. Ross

[57] ABSTRACT

A laser radar system capable of measuring windspeed to within 1 m/s at distances in the range of 10 km. The system comprises two fast atomic line filter-detectors, a first filter-detector and a second filter-detector, in which a metal vapor is excited by signal light and further excited to a Rydberg level by a pump laser beam. An electric field is applied to the filters which ionizes the atoms. The filter-detectors operate at one of the resonance absorption peaks of the metal vapor. The second filter-detector is also subject to a magnetic field which splits the absorption peak of the vapor into two absorption peaks leaving a valley in the position of the original absorption peak. A preferred lasing frequency range is a frequency range covering a portion of one of the slopes of the peak of the first filter and a portion of one of the opposite direction slopes of one of the peaks of the second filter. Within this range an increase in the frequency of signal light will result in a greater fraction of the light detected by one filter-detector and a smaller fraction detected by the other filter-detector and a decrease in the frequency of the signal light will have the opposite effect. In a preferred embodiment of this invention laser pulses from a laser operating near the midpoint of the preferred frequency range are beamed at a target which could be a windy portion of the atmosphere. Backscattered doppler shifted light from aerosols and particles in the atmosphere are collected by a telescope split into two parts, one part being directed to each filter-detector. The intensities of the light detected by the filter-detector are compared and the relative magnitudes are used to determine the windspeed in the direction of the laser beam. Pulses can be made very short and the travel time of the light is used to determine the range so that a map of windspeed as a function of range is provided in the direction of the laser beam.

10 Claims, 6 Drawing Sheets

LASER RADAR DEVICE

This is a continuation-in-part of application Ser. No. 07/422,671, filed Oct. 17, 1989, now U.S. Pat. No. 4,983,844. This invention relates to radar devices and in particular to laser radar devices useful for detection of windspeed.

BACKGROUND OF THE INVENTION

It is known that windspeed can be determined by transmitting a laser pulse into the wind and measuring the Doppler frequency shift of the light backscattered from aerosols and particles moving with the wind. The velocity of the wind $v_w$ in the direction of the laser pulse is:

$$v_w = \frac{f_s \lambda}{2}$$

where $f_s$ is the Doppler frequency shift and $\lambda$ is the wavelength of the laser pulse. Four proposed windspeed detection systems are discussed by Menzies in "Doppler lidar atmospheric wind sensors: a comparative performance evaluation for global measurement applications from earth orbit"; Applied Optics, Vol. 25, No. 15, Aug. 1, 1986. The principle challenge inherent in these systems is isolating the laser backscatter signal from background noise. These proposed systems utilize either a heterodyne detection system or a Fabry-Perot filter.

The narrowest optical filter bandwidths currently available with significant acceptance angles are obtained with atomic line filters (ALF's) which have acceptance bandwidths on the order of 0.001 nm. Broadband light containing narrowband signal light is passed through a color glass filter which cuts off wavelengths below a threshold value. The signal and remaining noise light enter an atomic vapor that only absorbs the signal light within the atom's 0.001 nm acceptance bandwidth thereby exciting those absorbing atoms to an intermediate energy level. A pump beam further excites these atoms to a second, higher energy level that then decays through various processes including fluorescence, to the ground state of the atom. The emitted fluorescence occurs at wavelengths below the threshold value. A second color glass filter then cuts off any wavelengths above the threshold which effectively permits passage of only the emitted narrowband fluorescence. In effect, the incoming signal has been internally shifted in wavelength to block any background radiation. For measurement of windspeed these filters have two drawbacks, slow response time (about 500 ns for the alkali atoms) and low quantum efficiency which is defined as the ratio of the number of fluorescence photons detected to the number of incoming signal photons.

It is known that an atom excited to a Rydberg level can be made to ionize quickly when subject to an intense electric field. And it is known that a resonance absorption peak can be split into multiple peaks by the application of a magnetic field.

SUMMARY OF THE INVENTION

The present invention provides a laser radar system capable of measuring windspeed to within 1 m/s at distance in the range of 10 km. The systems comprises two fast atomic line filter-detectors, a first filter-detector and a second filter-detector, in which a metal vapor is excited by signal light and further excited to a Rydberg level by a pump laser beam. An electric field is applied to the filters which ionizes the atoms. The filter-detectors operate at one of the resonance absorption peaks of the metal vapor. The second filter-detector is also subject to a magnetic field which splits the absorption peak of the vapor into two absorption peaks leaving a valley in the position of the original absorption peak. A preferred lasing frequency range is a frequency range covering a portion of one of the slopes of the peak of the first filter and a portion of one of the opposite direction slopes of one of the peaks of the second filter. Within this range an increase in the frequency of signal light will result in a greater fraction of the light detected by one filter-detector and a smaller fraction detected by the other filter-detector and a decrease in the frequency of the signal light will have the opposite effect. In a preferred embodiment of this invention laser pulses from a laser operating near the midpoint of this preferred frequency range are beamed at a target which could be a windy portion of the atmosphere. Backscattered doppler shifted light from aerosols and particles in the atmosphere are collected by a telescope and split into two parts, one part being directed to each filter-detector. The intensities of the light detected by the filter-detectors are compared and the relative magnitudes are used to determine the windspeed in the direction of the laser beam. Pulses can be made very short and the travel time of the light is used to determine the range so that a map of windspeed as a function of range is provided in the direction of the laser beam.

DETAILED DESCRIPTION OF PREFERRED EMBODIMENTS

The present invention can be described by reference to the drawings.

DESCRIPTION FAST ATOMIC LINE FILTER

Figure 1:
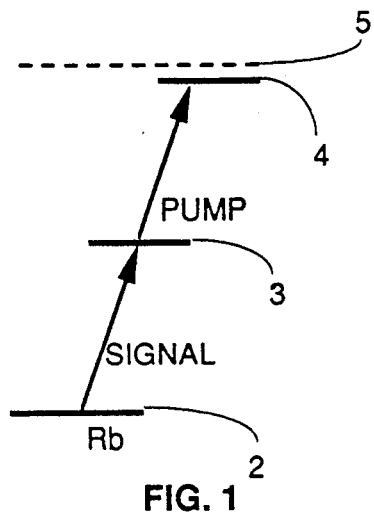
FIG. 1 is a general energy level diagram for the fast atomic line filter-detector.

FIG. 1 is a simplified energy level diagram for operation of a fast atomic line filter. In this case potassium (K) is used as the active medium. The operation of the filter is based on the following sequence of events. A photon to be detected excites K atom from the ground state 2 to an intermediate energy level 3. This atom is then further excited by a pump photon to a Rydberg level 4 Stark shifted by an applied electric field. The electric field then causes the atom to ionize in a short time compared to 1 ns. (The addition of this electric field speeds up the response time of the atomic line filter by more than two orders of magnitude.) The filter can be designed for the detection of the resulting ions or electrons.

Figure 2:
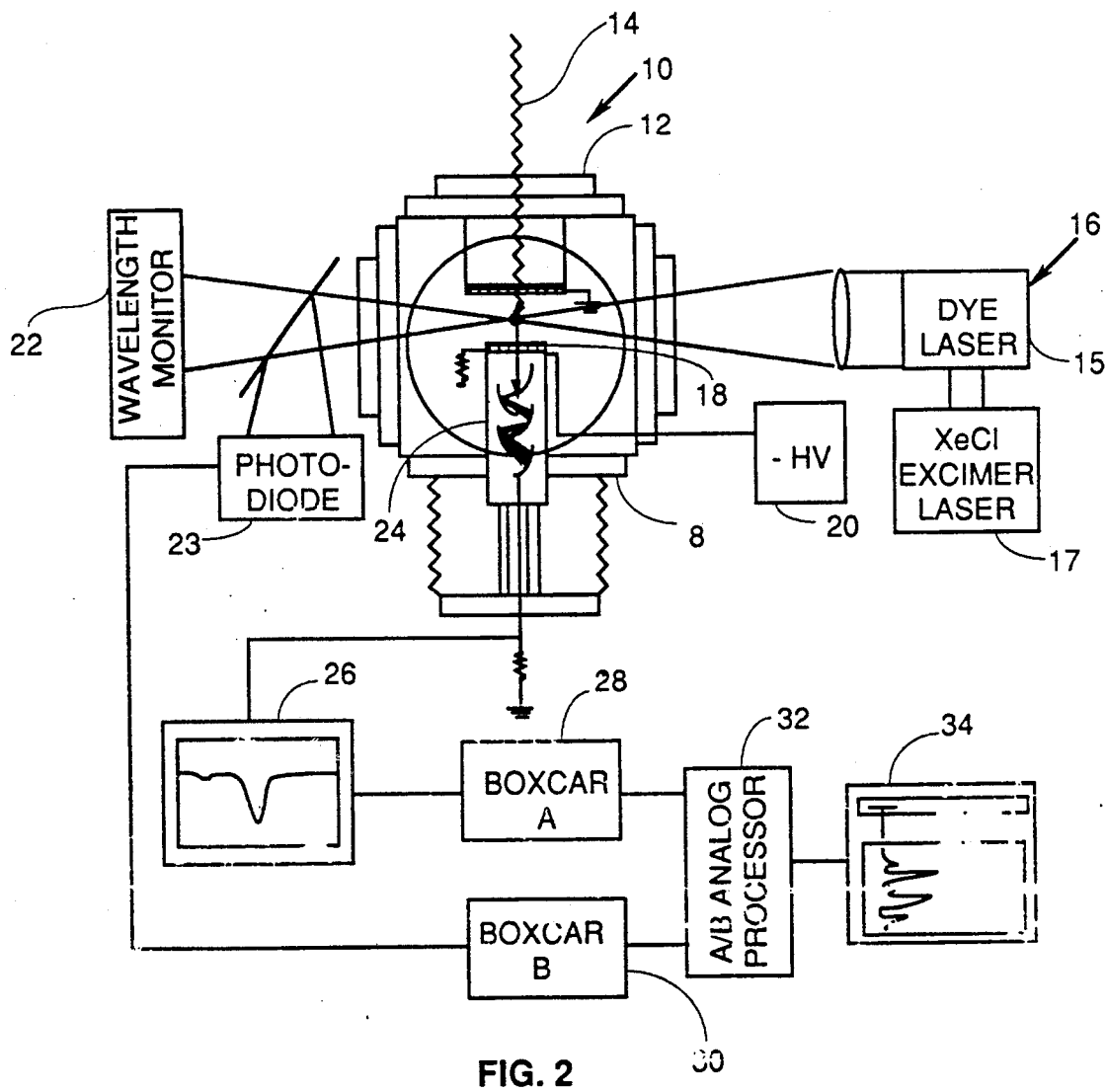
FIG. 2 is a schematic diagram showing the elements of a fast atomic line filter-detector.

A fast filter-detector device is shown schematically in FIG. 2. A vacuum chamber 8 contains K vapor at a temperature of about 150° C. and pressure of about $10^{-4}$ torr. The chamber contains an aperture 10 covered by a color glass filter 12 chosen to cut off wavelengths shorter than about 700 n. Signal light 14 at about 770 nm passes through filter 12. Photons from the signal light excite the K atoms to intermediate level 3 as shown in FIG. 1. Light from a pulsed narrowband (<1 GHz) dye laser pump 16 (comprised in this case of excimer laser 17 and dye laser 15) operating at about 464 nm further excites the K atoms from level 3 to a Rydberg level 4, also shown in FIG. 1, which is Stark shifted by a negative 2 kV potential applied to grid plate 18 by high voltage source 20. These atoms then ionize in a time short compared to 1 ns. Monitor 22 used to ensure that that pump laser is turned to the correct wavelength and photodiode 23 measures the pump laser intensity. The resulting ions are accelerated toward grid plate 18 and then impact on the first dynode of electron multiplier 24 creating secondary electrons which are in turn multiplied by the subsequent stages of the electron multiplier. In effect about $10^6$ electrons are produced per single ion entering the multiplier providing a detectable signal at the output of the multiplier.

Oscilloscope 26 provides a real time picture of the multiplier voltage. The boxcar averagers 28 and 30, sample both the multiplier signal and the pump laser intensity. Their outputs are fed into analog processor 32, which divides the multiplier signal size by the pump laser intensity providing a normalized output signal and the result may be displayed on chart recorder 34.

ZEEMAN EFFECT

Figure 3:
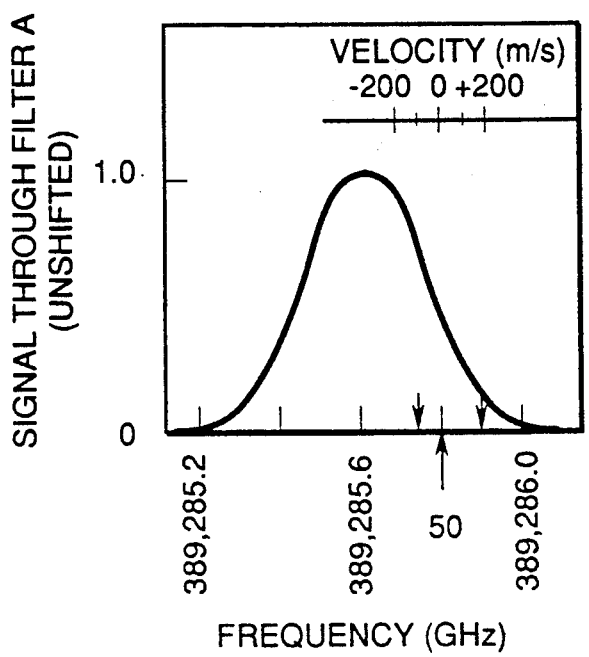
FIG. 3 is a graph of a resonance peak.
Figure 5:
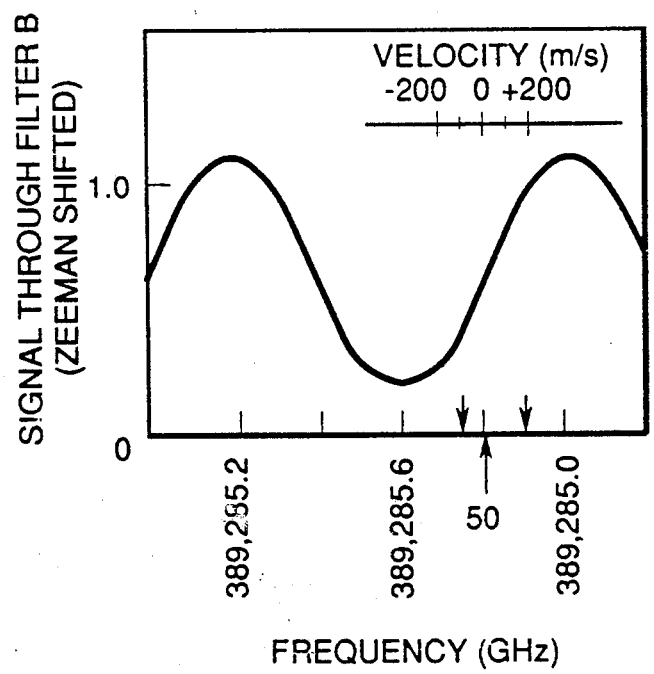
FIG. 5 is a graph of a Zeeman shifted resonance peak split into two peaks.
Figures 4A, 4B, 4C, 4D, 4E:
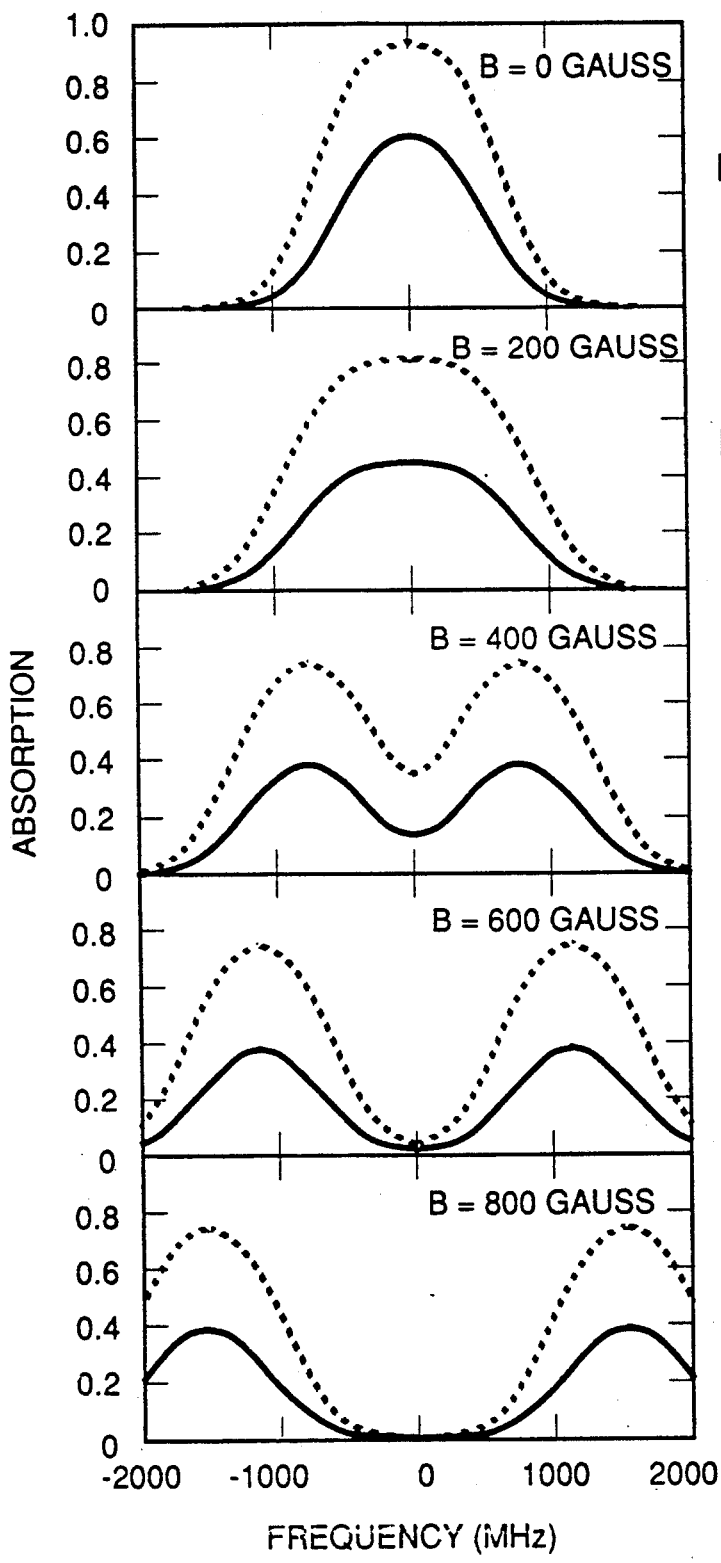
FIGS. 4a-4e comprise a set of graphs demonstrating the Zeeman effect.

The filter depicted in FIG. 2 is effective in filtering all light outside a bandwidth of roughly 800 MHz around the potassium 769.9 nm absorption peak. (i.e. outside the range of about 389,285.6±0.4 GHZ; 769.9±0.0005 nm) The shape of the curve of the portion of light passing through the filter as a function of frequency is shown in FIG. 3. The peak is at 769.9 nm (389,285.6 GHz). A magnetic field when applied to an absorption cell will cause a shifting of the shape of this curve. This effect is shown qualitively in FIG. 4 for magnetic fields of 0, 200, 400, 600 and 800 Gauss. We have shown in FIG. 5 a preferred shape of the curve corresponding to about 600 Gauss. We have labeled the absissa on both FIG. 3 and FIG. 6 to show frequency and the arrow designated 50 locates a preferred frequency of the transmitted laser pulse which is 389,285.8 GHz. As can be seen from an examination of FIGS. 3 and 5, light at the transmitted frequency of 389,285.8 GHz will result in approximately equal signal through both filter A and filter B. However, a slight increase in the signal frequency from 389,285.9 GHz will result in an increase in the signal through filter B and a decrease in the signal through filter A. A decrease in the signal frequency will have the opposite effect.

Figure 6:
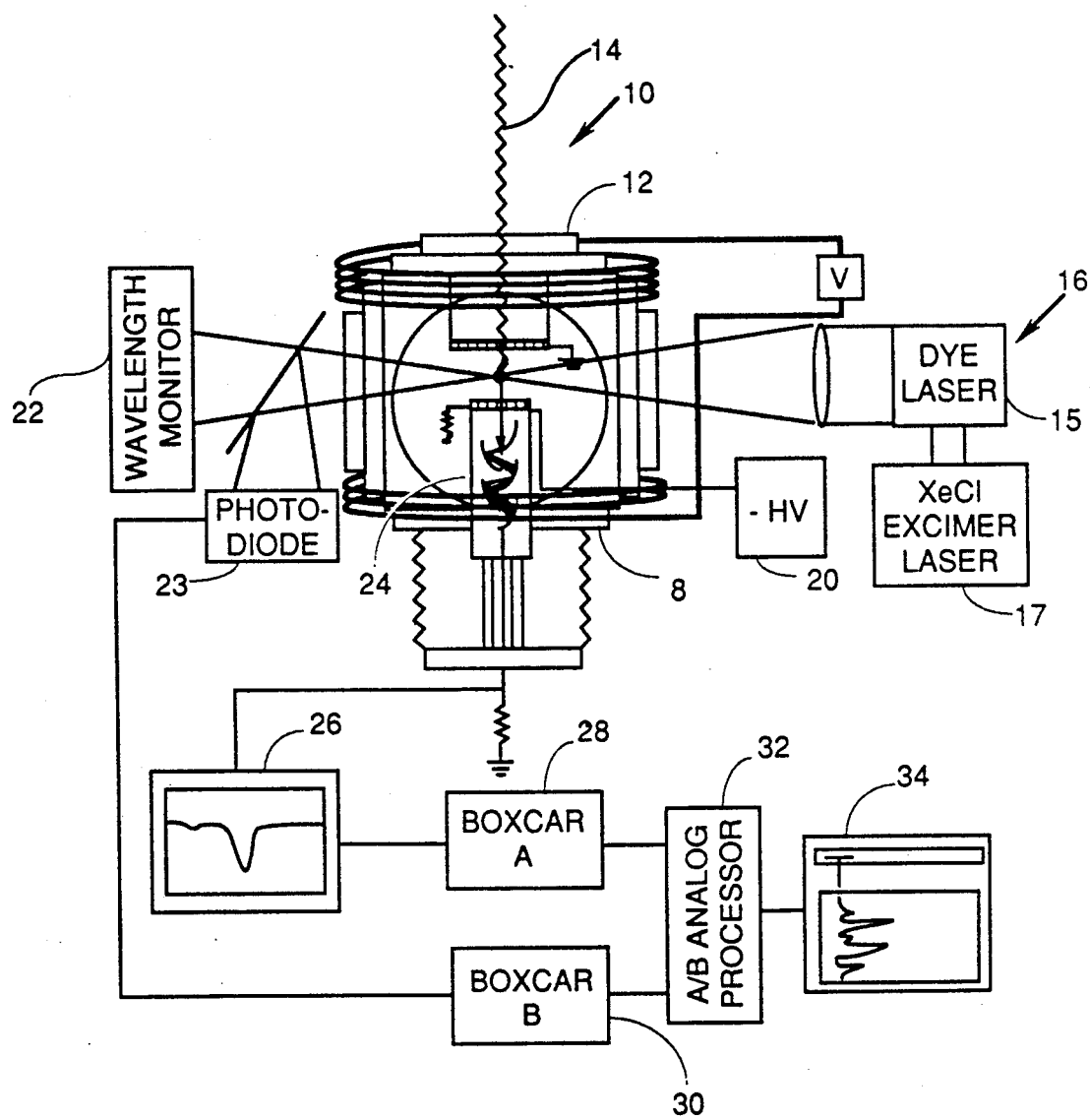
FIG. 6 is a schematic diagram of the elements of a Zeeman shifted fast atomic line filter-detector.

We have shown in FIG. 6 a schematic diagram of a Zeeman shifted fast atomic line filter. It is essentially the same as the fast atomic line filter shown in FIG. 2 except that a coil 43 places the potassium vapor in a magnetic field of about 600 Gauss.

SYSTEM FOR MEASURING WINDSPEED

Figure 7:
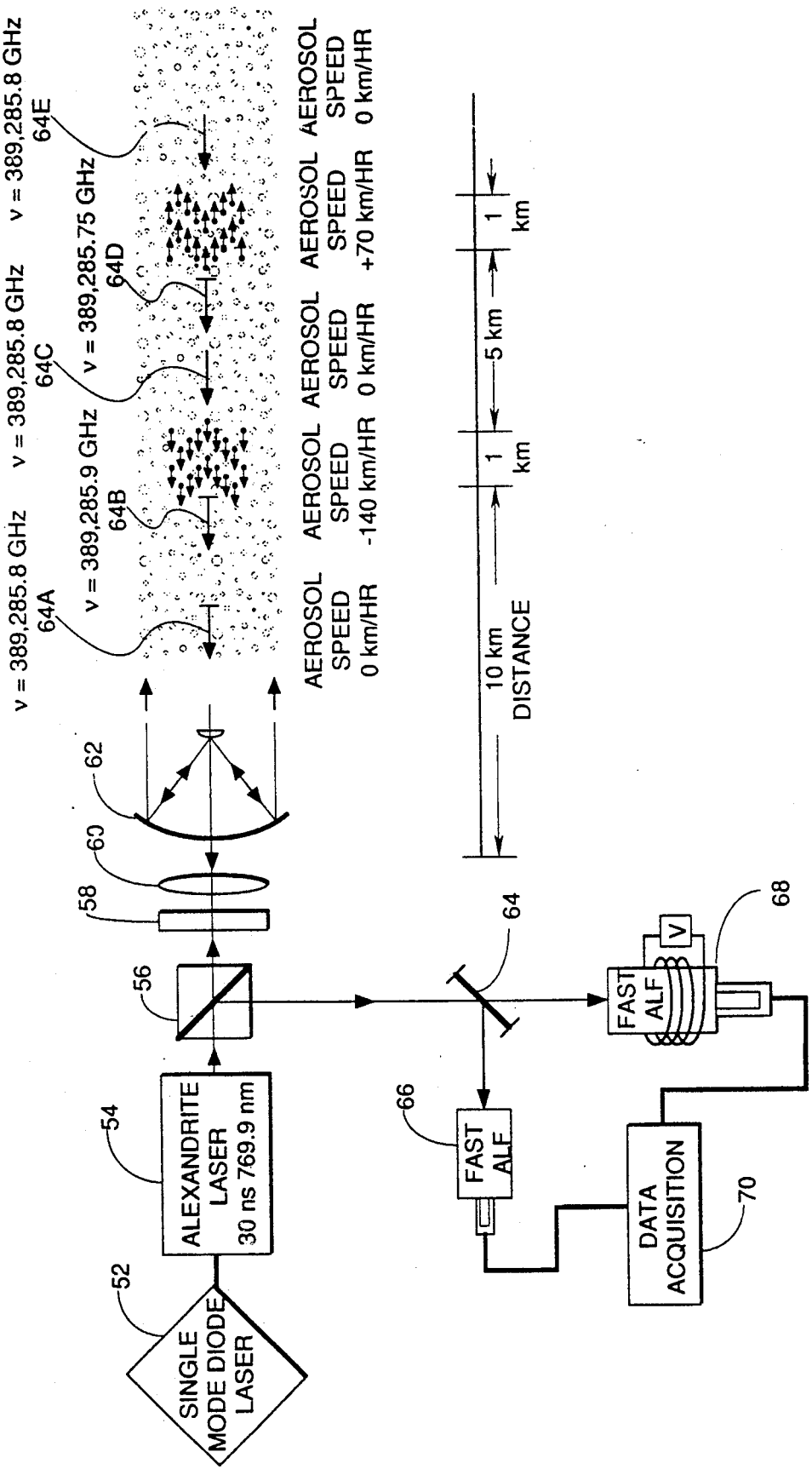
FIG. 7 is a chart demonstrating the present invention in operation.
Figure 8A:
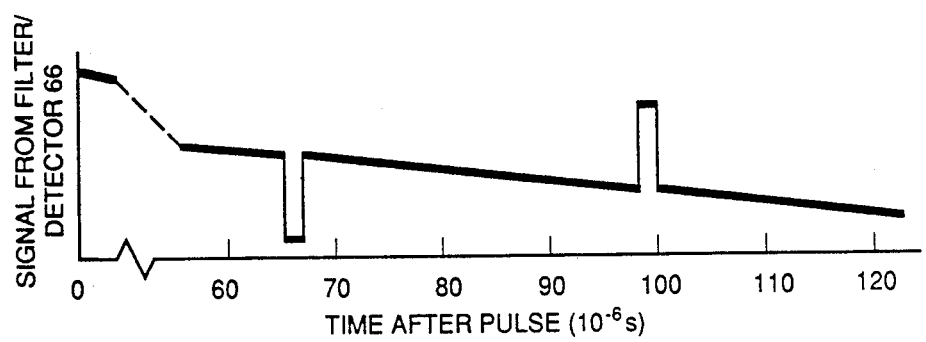
FIGS. 8a-8c comprise a set of graphs indicating the data obtained in the situation depicted in FIG. 7.
Figure 8B:
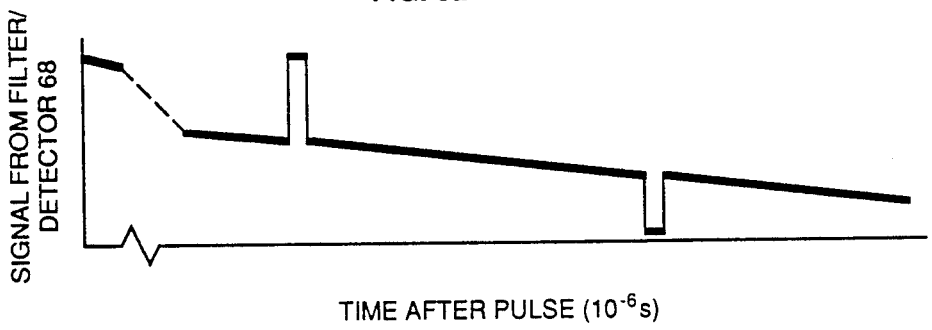
Figure 8C:
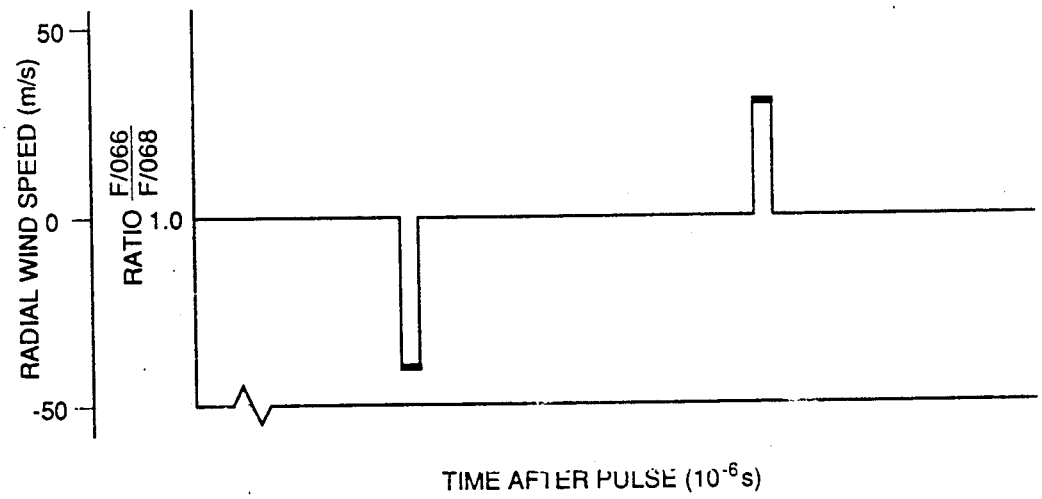

A system for measuring windspeed is shown in FIG. 7.

A single mode diode laser 52 provides photons at 769.9 nm. This laser provides the seed photons for a flashlamp pumped, narrowband, Q-switched, Alexandrite laser 54. The pulses from laser 54 are 0.5 Joule and the repetition ratio is 20 pulses per second. This laser system is available commercially from Light Age, Inc. and is marketed as PAL system. The nominal frequency is controllable within the range of interest, i.e. around 389,285.6 GHz and the bandwidth is less than 0.1 GHz.

The pulses from laser 54 passes through polarizing beamsplitter cube 56, and its polarization is rotated 45° by $\pi/4$ Faraday rotator 58. It then passes through relay optics 60 to ½ meter aperture telescope 62 which directs the beam to the desired azimuth and elevation angles. A portion of the beam is immediately retro-reflected into fast ALF detectors 66 and 68 to provide a zero Doppler shift calibration. (The backscattered photon's polarization is rotated an additional 45° so that the received signal is directed to the detectors by the polarizing beamsplitter cube 56).

The laser pulses travel through the atmosphere and a small portion is backscattered from aerosols and particles in the atmosphere as indicated by the large arrows 64A, 64B, 64C, 64D, and 64E shown in FIG. 7. Where the speed of the air in the direction of the beam is zero as depicted for 64A, 64C and 64E the frequency of the backscattered light is the same as the transmitted beam i.e. 389,285.6 GHz. At 64 B the air is depicted as moving with a speed of 140 Km/Hr (38.9 m/s) in a direction opposite the beam. The light backscattered from aerosols in this section of the atmosphere will be increased in frequency by approximately 0.1 GHz or 100 MHz this results from:

$$f_s = \frac{2v_w}{\lambda} = \frac{(2)(-140 \times 10^3 \text{ m})}{(769.9 \times 10^{-9} \text{ m})(3600 \text{ s/hr})} = 100 \text{ MHz}$$

Similarly, at 64D the aerosols are depicted as moving in the direction of the laser pulses at a speed of 70 Km/Hr and as a result the backscatter would be shifted in frequency downward by 50 MHz. The doppler shifted frequencies are indicated by downward arrows on FIGS. 3 and 5.

Since location 64B is about 10 Km from the laser it will take about $66 \times 10^{-6}$ sec for the light to travel from the laser to location 64B and back to detectors A and B. The time to get to location 64D and back is about $100 \times 10^{-6}$ sec. The absolute value of the returning signal will decrease roughly by the second power of the distance traveled and an exponential term that depends upon the clarity of the air.

The backscatter light is collected by telescope 62 and directed through relay optics 60, rotator 58, beamsplitter 56 to 50-50 beamsplitter 64 where one half of the beam is directed to unshifted fast ALF detector 66 which is of the type described in FIG. 2 and one half is directed to Zeeman shifted fast ALF detector 68 which is the type described in FIG. 6. The outputs of the two filter detectors feed data acquisition unit 70 which compares the outputs as a function of time to determine the windspeed as a function of radial distance from the detector system.

Qualitive plots of the outputs of filter-detector 66 and 68 and the ratio of the signal from filter-detector 66 to the signal from filter-detector 68 are shown in FIG. 7.

For our preferred embodiment 20 ns data gates are correlated with the pulse rate of 20 Hz. Since the pulse length of this preferred system is about 30 ns, range can be determined to within an accuracy of about 15 feet.

The unique aspect of this device is the precision frequency measurements possible with a pair of atomic line filter-field ionization detectors at least one of which is Zeeman shifted. There are several other applications for these detectors. Windspeed measurement has already been mentioned, so it is clear that anything that scatters light can have its velocity determined with this invention. Also long range optical communication is an obvious extension of the technology, only photons in-band are detected and the band may be tuned via the magnetic field. Covert point-to-point optical communication is another obvious extension. The crossover point between the detectors may be utilized for detecting small modulations in a laser beam. The frequency modulations are easily decoded into data but no other type of detector can receive them.

The reader should construe the above described embodiment of this invention as examples and the scope of this invention shall be determined by the appended claims and their legal equivalents.

We claim:

1. A speed determining laser radar device comprising:
    (a) a laser means for transmitting to a target or targets a narrowband laser beam, defining a nominal wavelength of said transmitted beam,
    (b) a first fast atomic line filter-detector comprising:
        a first sealed chamber having an aperture for the passage of signal light into the interior of said container,
        a gas contained in said sealed chamber, the atoms of said gas having a specific resonance energy level approximately equal to the nominal wavelength of said transmitted beam and a Rydberg level, said resonance energy level defining a resonance peak,
        a pump means for exciting the atoms of said gas from said specific energy level to said Rydberg level,
        a high voltage means for creating an electrical potential across all or a portion of said gas said electrical potential being high enough to ionize essentially all; atoms of said gas excited to said Rydberg level, and
        a detection means for detecting ionization events,
    (c) a second fast atomic line filter-detector comprising all of the above elements of said atomic line filter-detector and also comprising a magnetic means for subjecting the atoms of said gas to a magnetic field in order to cause a Zeeman shift to said resonance peak into two resonance peaks,
    (d) a data acquisition and comparison means for acquiring and comparing the amplitudes of the outputs of said first and second filter-detector to determine the speed of said target or targets based on frequency shift from said nominal wavelength of the laser light reflected from said target or targets.

2. A laser radar device as in claim 1 wherein said laser beam is a pulsed beam and said data acquisition and comparison means is further adapted to determine the range of said target or targets based on the period of time required for light from said laser beam to travel from said laser means to said target or targets and back to said first and second detectors.

3. A laser radar device as in claim 1 wherein said device is adapted to determine speed of said targets at many locations along the length of said laser beam.

4. A laser radar device as in claim 3 wherein said device is adapted to measure windspeed at many locations along the length of said laser beam.

5. A laser radar device as in claim 1 wherein said detector means for detecting ionization events comprises an electron detector.

6. A laser radar device as in claim 1 wherein said detector means for detecting ionization events comprises an ion detector.

7. A laser radar device as in claim 1 wherein said electron detector means comprises an electron multiplier.

8. A laser radar device as in claim 1 wherein said gas is chosen from a group consisting of lithium, sodium, potassium, rubidium and cesium.

9. A laser radar device as in claim 2 wherein said gas is potassium.

10. A laser radar device as in claim 3 wherein said pump means comprises a laser device capable of producing a laser beam at about 464 nm.

* * * * *